(12) United States Patent
Jörneus

(10) Patent No.: US 6,827,575 B1
(45) Date of Patent: Dec. 7, 2004

(54) METHOD, ARRANGEMENT AND USE FOR APPLYING A SPACER TO AN IMPLANT BY MEANS OF A SCREW

(75) Inventor: Lars Jörneus, Frillesås (SE)

(73) Assignee: Nobel Biocare AB, Göteborg (SE)

( * ) Notice: Subject to any disclaimer, the term of this patent is extended or adjusted under 35 U.S.C. 154(b) by 0 days.

(21) Appl. No.: 09/936,722

(22) PCT Filed: Feb. 24, 2000

(86) PCT No.: PCT/SE00/00359

§ 371 (c)(1),
(2), (4) Date: Jan. 31, 2002

(87) PCT Pub. No.: WO00/54697

PCT Pub. Date: Sep. 2, 2000

(30) Foreign Application Priority Data

Mar. 18, 1999 (SE) .............................................. 9900967

(51) Int. Cl.[7] .................................................. A61C 3/00
(52) U.S. Cl. ...................................................... 433/174
(58) Field of Search ................................ 433/173, 174, 433/141

(56) References Cited

U.S. PATENT DOCUMENTS

| | | |
|---|---|---|
| 5,145,371 A | 9/1992 | Jörneus |
| 5,322,443 A | 6/1994 | Beaty |
| 5,368,160 A * | 11/1994 | Leuschen et al. ........... 206/339 |
| 5,437,550 A | 8/1995 | Beaty et al. |
| 5,462,436 A | 10/1995 | Beaty |
| 5,564,924 A * | 10/1996 | Kwan .......................... 433/173 |
| 5,622,500 A * | 4/1997 | Niznick ....................... 433/173 |
| 5,692,904 A | 12/1997 | Beaty et al. |
| 5,944,525 A * | 8/1999 | Ura .............................. 433/173 |
| 6,068,480 A * | 5/2000 | Misch et al. ................. 433/173 |
| 6,083,004 A * | 7/2000 | Misch et al. ................. 433/173 |
| 6,159,008 A * | 12/2000 | Kumar ........................ 433/163 |
| 6,217,332 B1 * | 4/2001 | Kumar ........................ 433/173 |
| 6,247,932 B1 * | 6/2001 | Sutter ......................... 433/173 |
| 6,261,097 B1 * | 7/2001 | Schmutz et al. ............. 433/173 |
| 6,312,260 B1 * | 11/2001 | Kumar et al. ............... 433/174 |

FOREIGN PATENT DOCUMENTS

| | | |
|---|---|---|
| EP | 0419431 | 3/1991 |
| WO | 95/24163 | 9/1995 |

* cited by examiner

Primary Examiner—Ralph A. Lewis
(74) Attorney, Agent, or Firm—Venable LLP; Eric J. Franklin

(57) ABSTRACT

A method for securing a spacer to an implant integrated in bone. A spacer and a screw are engaged with a holder in a rotationally fixed position with respect to the holder. The spacer is engaged in a spacer engaging portion of the holder and the screw is engaged in a screw engaging portion of the holder. The screw is inserted in a threaded receiving passage of the implant such that threads on the screw engage threads of the receiving passage. A rotational motion is applied to the holder, thereby rotating the rotationally fixed spacer and screw and screwing the screw into the receiving passage of the implant. A cooperation between a bearing surface of the spacer and a top surface of the implant is established at a predetermined position of screwing. The holder is separated from the spacer and the screw.

34 Claims, 2 Drawing Sheets

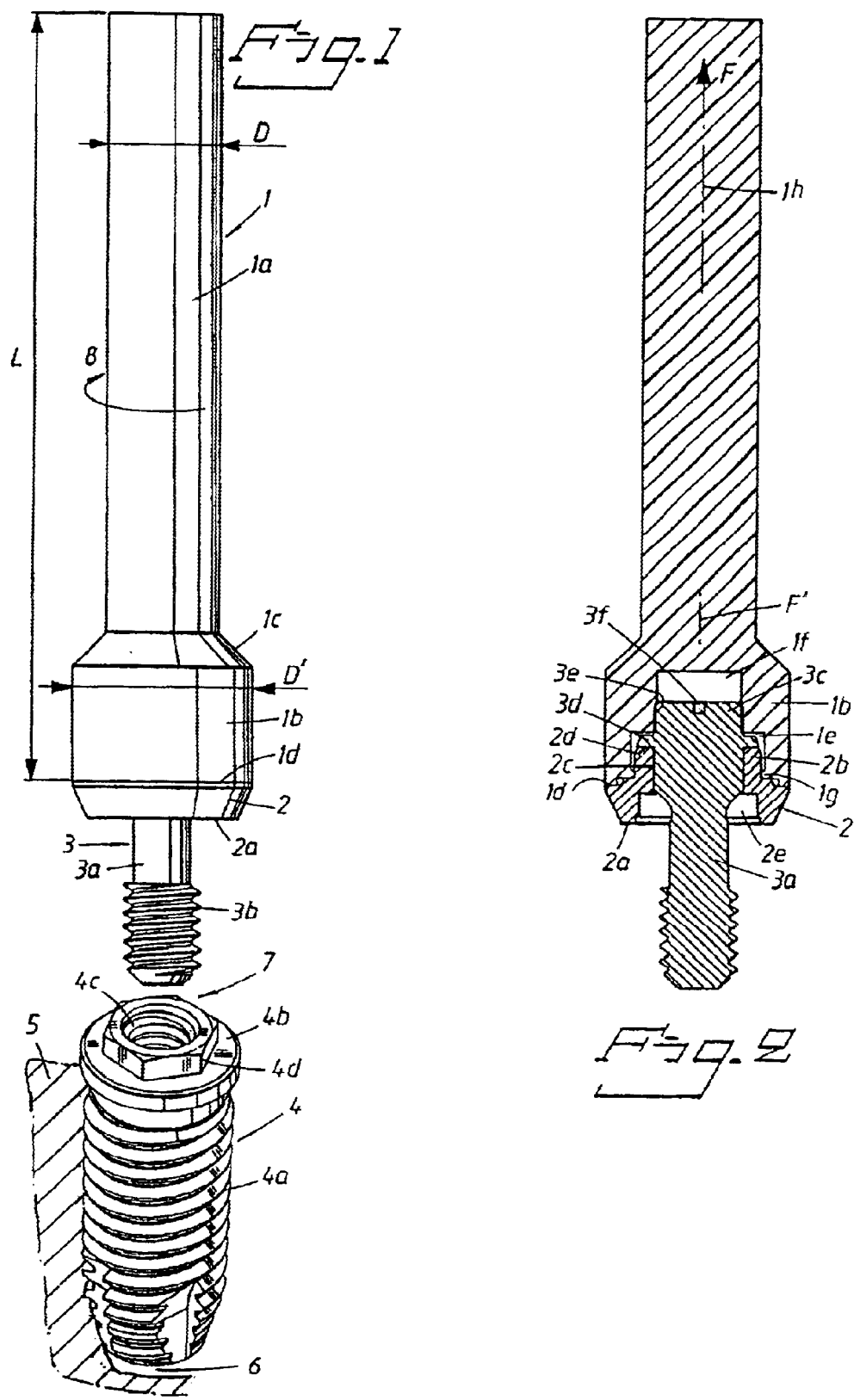

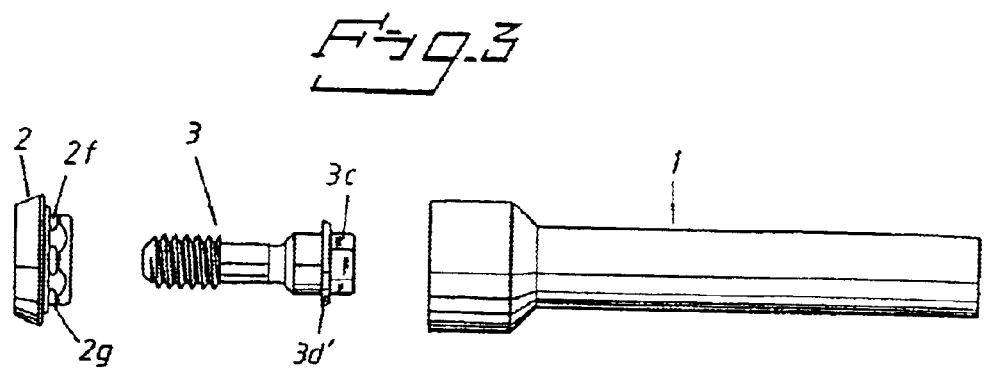
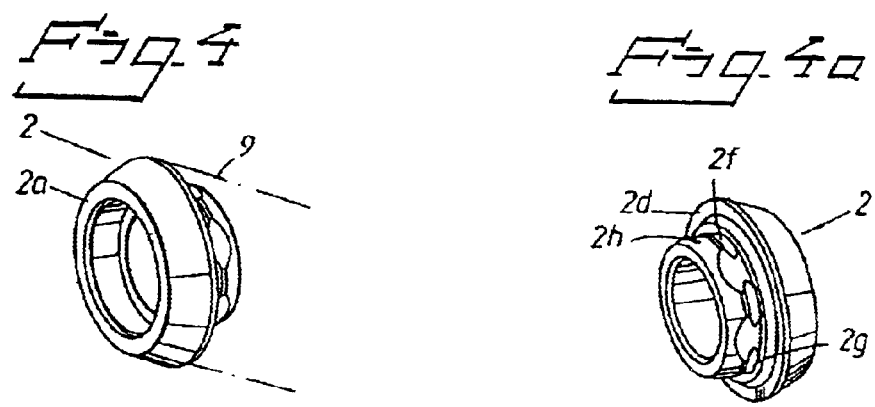
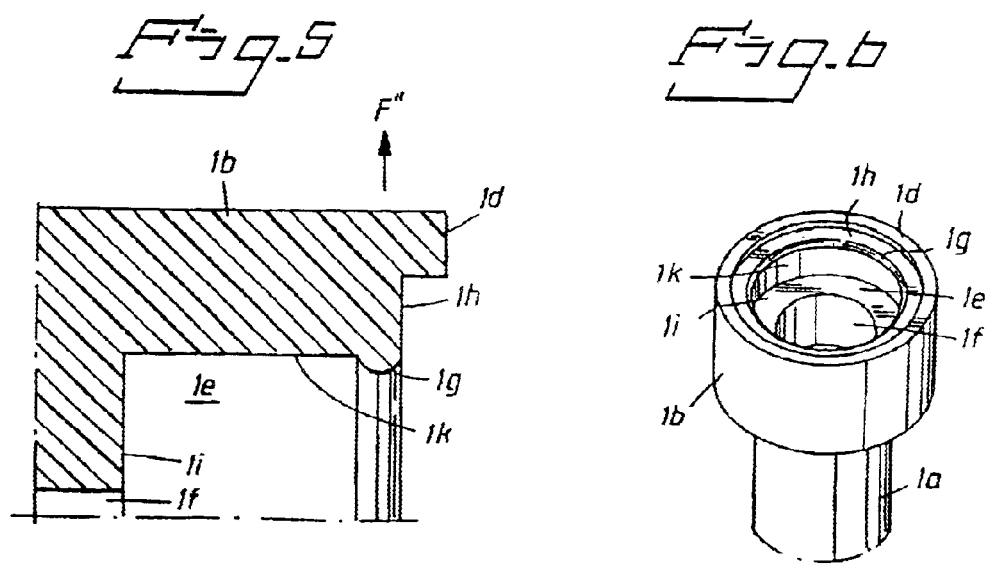

METHOD, ARRANGEMENT AND USE FOR APPLYING A SPACER TO AN IMPLANT BY MEANS OF A SCREW

FIELD OF THE INVENTION

The present invention relates to, inter alia, a method for securing a spacer to a firmly integrated implant, preferably in the jaw bone, by means of a holder and with the aid of a screw. The threaded part of the screw will extend through a recess in the spacer so that its thread cooperates with the thread of the implant. The screw head can moreover cooperate with a tightening and locking surface in the spacer, which also has a bearing surface which can cooperate with a top surface of the implant. The invention also relates to an arrangement for application of this method. The invention relates in addition to the use of the holder for securing a spacer in an implant by means of a screw.

BACKGROUND OF THE INVENTION

After the implant has become firmly integrated in the bone, which normally takes 3 to 6 months after fitting the fixture or implant, a spacer is attached. In this connection, an incision is made through the gum so that the upper surface of the implant is exposed.

Upon attachment of the spacer, which is also called the spacer element, the latter is screwed securely to the implant or fixture. The spacers which are normally used here are made up of an essentially cylindrical component which is to be screwed securely with a loose, separate screw. In the majority of cases, the spacer has an internal hexagon which is intended to match a corresponding external hexagon on the upper part of the implant. There are also spacer designs in which the actual spacer body and the screw have been integrated to form one unit. However, it is advantageous to be able to use screw and spacer as two separate units. The tightening of the screw can then be improved by virtue of the fact that the frictional torque acting on the screw head is reduced because the contact radius of the screw head is less compared to the case of using separately integrated spacer and screw. In addition, when the screw and spacer form different units, they can be made of different materials. The spacer is preferably made of a tissue-compatible material, for example titanium or a ceramic material. The screw can be made of stronger material and can be coated with a friction-reducing coating so as to obtain an improved pre-stressing of the screw connection. An alternative here, or complement, is to choose a screw material which itself affords low friction between the thread of the screw and the corresponding internal threading of the implant. Such material can, for example, include certain gold alloys.

In purely general terms, it is relatively difficult to handle small spacer and screw components in or around the oral cavity, for lack of space among other reasons. Various attempts have been made to make handling and securing of spacer and screw easier. For example, a special counterstay has been used which is arranged on the spacer at the same time as a screwdriver is engaged in the groove of the screw head. There are also examples of so-called pre-fitted disposable spacer holders which consist of two mutually movable parts, one of which engages round the screw and the other round the spacer.

In connection with the said known prior art, reference may be made to U.S. Pat. Nos. 5,145,371, 5,322,443, 5,462,436, 5,437,550 and 5,692,904.

There is in general a great need to be able to handle small spacer and screw components in accordance with the above. In this context, it is important to be able to make available methods, arrangements and uses which are technically simple to implement and to use.

Thus, for example, problems arise when using special counterstays which are arranged on the spacer, since the support capacity is relatively poor and the components are not pre-assembled but are applied by the operators or their assistants during the operation. Using holders with mutually movable parts represents a technically complicated and awkward solution which is not compatible with practical handling and use.

SUMMARY OF THE INVENTION

The object of the invention is, inter alia, to solve these problems, and the feature which can principally be regarded as characterizing a method according to the invention is that the screw, in its position passing through the spacer, and the said spacer are first held together in a rotationally fixed manner in the holder, so that the bearing surface of the spacer protrudes beyond the holder, and the threaded part of the screw in turn protrudes beyond the bearing surface. Further features are that the rotationally fixed unit thus established by the holder, the spacer and the screw is thereafter applied to the implant in a position of cooperation of the threads of the implant and screw. The unit is then given rotating movements, during which the thread of the screw is screwed down into the thread of the implant. At a predetermined position of screwing, preferably where the cooperation between the bearing surface of the spacer and the top surface of the implant has been established, the holder is separated or detached from the spacer and the screw by means of a separating movement, for example a deflecting movement, which is preferably distinct from the rotating movement. The screw head is exposed for possible further tightening.

In one embodiment, the novel method is characterized by the fact that in order to achieve the holding function for holder, spacer and screw to form a common rotationally fixed unit, the screw is applied in the spacer to a position where its head bears against the aforementioned tightening and locking surface of the spacer, and by the fact that the spacer and screw thus combined are thereafter pressed into an end recess in the holder, or the holder is pressed over the spacer and the screw via the said recess. In one embodiment, the holder works with an elastic and/or spring function and/or snap-in function, by means of which the spacer and the screw, in their coupled positions, are locked to the holder in the direction of rotation. While it is being screwed in, the spacer is preferably brought into cooperation with the top surface of the implant only via an annular end surface, i.e. hexagonal or other types of effective, rotation-fixing surfaces are not present in this illustrative embodiment.

The feature which can principally be regarded as characterizing an arrangement according to the invention is that before the screw is introduced into the thread of the implant, the holder supports the screw in its position passing through the spacer and supports the spacer in a rotationally fixed manner, with the bearing surface of the spacer protruding beyond the holder, and the threaded part of the screw protruding beyond the bearing surf ace. Further characteristics are that a rotationally fixed unit thus established by the holder, the spacer and the screw can be applied to the implant in a position of cooperation between the threads of the implant and of the screw, where screwing of the screw thread into the implant thread can be effected by means of rotating or screwing movements of the unit. A further characteristic is that the holder, in a possible screwing position, preferably where the bearing surface of the spacer cooperates with the top surface of the implant, is arranged to be separable from the spacer and the screw by means of separating movements which are preferably distinct from the rotating movement, whereupon the screw head is exposed for possible further tightening. The said separation can be effected by means of the deflection function in the holder (the present holder part).

In one embodiment of the novel arrangement, the holder, at least in its part which can cooperate with the spacer and the screw, is made of plastic or other elastic material. The spacer and the screw, in the said coupled position, can be applied in an end recess in the said holder part receiving the screw and the spacer via a function preventing reciprocal rotating movements between spacer, screw and holder, which, can be obtained from guide surfaces, a spring function, snap-in function, etc. In a further embodiment, the holder or holder part is provided with a first recess for the screw head and a second recess for securing parts on the spacer. The holder can be applied on the securing part and the screw head and secures the spacer and the screw by means of the in-built spring function and/or elasticity in the wall-supporting material of the first and second recesses, possibly in combination with a snap-in function. The holder can consist of or comprises an elongate element made of plastic or equivalent material. The holder is comparatively easily separable from the spacer and the screw, in their position applied in or firmly screwed to the implant, by means of a withdrawal movement or withdrawal movements essentially coinciding with the longitudinal direction of the implant or with a tilting movement, in which the holder disengages (for example springs aside) from the said securing part and head on the spacer or the screw. In a further embodiment, the spacer can be provided with an annular bearing surface without internal guide surfaces, for example internal guide surfaces in the form of square or hexagonal or polygonal surfaces. The holder and its attachment to the spacer and the screw can further be arranged to permit a first anchoring contact between the top surface of the implant and the bearing surface of the spacer which eliminates the risk of loosening of the implant in the bone (dentine). After the holder is detached from the spacer and the screw, the latter can be tightened for obtaining a second anchoring contact which is effected with a force which considerably exceeds the force for the first anchoring contact. The secondary tightening function is effected in a manner known per se with a screwdriver of conventional type in this context. For the second anchoring contact, a counterstay function in the spacer can be used. For this, a tool is used which retains the spacer in a defined angular position while the screw is acted upon by the screwdriver or equivalent. The thread of the screw can be made of relatively strong material and/or coated with a friction-reducing coating for the purpose of improving the anchoring stress between spacer, screw and implant.

The thread diameter of the screw can be chosen such that it is substantially less than the diameter of the bearing surface. For example, the thread diameter of the screw can be half the diameter (mean diameter) of the bearing surface. By choosing the diameter of the screw thread and the diameter of the bearing surface and by choosing low-friction material and/or low-friction coating, the coefficient of friction is substantially lower, for example half as great at the thread as it is at the bearing surface. This means that a secure counterstay (i.e. no risk of loosening of the implant relative to the dentine) can be applied against the outside of the spacer in conjunction with the secondary tightening, despite the absence of mechanical locking via active locking surfaces between spacers and implant.

An arrangement can principally be characterized by the fact that the holder supports the spacer and the screw in a rotationally fixed manner, with the bearing surface of the space protruding beyond the holder, and with the screw extending through the spacer and protruding beyond the bearing surface via its threaded part.

The holder is preferably designed with an end recess or end recesses in which the spacer and the screw head are pressed and held by the spring function and/or the elasticity of the holder and possibly the snap-in function. Together with the spacer and the screw, the holder forms a rotationally fixed unit which facilitates the application to the implant and the handling and delivery of the spacer and the screw.

A use according to the invention can principally be regarded as being characterized by the fact that the holder used is an elongate element which supports the spacer and the screw in their coupled position in a rotationally fixed manner, with the bearing surface of the spacer against the implant protruding beyond the holder, and the threaded part of the screw in its turn protruding beyond the bearing surface.

Further refinements of the use are characterized in that a resilient and/or elastic part of the holder is used for gripping around and securing the spacer and the screw in rotationally fixed positions in relation to the holder and to each other. The holder can also be used for transmitting manual rotational movements to the screw as the latter is screwed into the implant, i.e. as a shaft.

By means of what has been proposed above, a number of advantages are obtained which solve, inter alia, the problems set out by way of introduction. The spacer and the spacer screw can be joined together with a holder made, for example, of plastic which is clamped by means of the spring function in the holder part or snapped securely on the spacer and the screw so that these three components are held together in a simple manner. The underside of the spacer can be designed without the hexagonal socket which is generally used in this context. The underside of the spacer can thus be designed as a recess of circular cross section, which renders production much less expensive. This means that the spacer element can be rotated down to the correct position on the fixture in a much simpler way compared to what was possible previously. The advantages of the present invention are primarily that it is now necessary to handle just one element, which can be easily designed to facilitate handling of spacer and screw as such. In addition, it is no longer necessary to depend on the spacer having to assume a rotationally correct position with respect to the implant. The holder can easily be removed and the final tightening made. If so required, a counterstay can be applied during tightening. This is often essential in order not to unnecessarily load the interface between bone and fixture so that the fixture risks being dislodged from its position. On first analysis, one may be led to believe that tightening with a counterstay is not possible because of the lack of rotational locking using hexagons or other polygons. More detailed analysis reveals that as long as the available frictional torque between fixture and spacer is greater than the frictional torque acting on the implant via the screw, i.e. the so-called thread torque, a counterstay can be applied to the spacer. The frictional torque which is transmitted to the fixture on the spacer screw depends on the tensile force in the screw, the diameter of the screw and the coefficient of friction between the screw thread and the internal thread of the fixture. The counterstay torque which can be applied depends on the clamping force between spacer and fixture which is the same as the tensile force of the screw, the diameter of the bearing surface and the coefficient of friction between the spacer and the top surface of the fixture.

BRIEF DESCRIPTION OF THE DRAWINGS

Presently proposed embodiments of the method, arrangement and use having the characteristics of the invention will be described below with reference to the attached drawings, in which:

FIG. 1 shows, in a side vies and partial perspective view, the holder, spacer and screw in relation to an implant, FIG. 2 shows a longitudinal section through the holder, spacer and screw, in the assembled position, FIG. 3 shows a side view of the holder, screw and spacer, in the disassembled position, FIGS. 4 and 4a are perspective views of the spacer, viewed obliquely from below and from above, respectively, and FIGS. 5 to 6 show part of the holder in longitudinal section and enlarged.

DETAILED EMBODIMENT

In FIG. 1, a holder is indicated by 1. The holder comprises an elongate part 1a and a widened part 1b arranged on the elongate part. The holder can be made of plastic material, the part 1a can be a substantially solid part and the part 1b has an end recess, in accordance with what is described below. The holder has a length L of about 20 mm and a diameter D of about 3 mm in part 1a. The part 1b has a diameter D' of about 5 mm. The parts merge into each other via a bevel 1c. Applied to the holder in a rotationally fixed manner there is a spacer 2 which protrudes beyond the end surface 1d of the holder via a part which has a bearing surface 2a. In accordance with what is described below, a screw is applied to the holder and extends through a recess in the spacer so that its threaded part protrudes beyond the bearing surface 2a. The screw is indicated by 3 and the threaded part of the screw by 3a, while the thread itself is indicated by 3b. FIG. 1 also shows an implant or fixture 4 which has become firmly integrated in a bone, preferably in a symbolically indicated dentine 5. The implant or the fixture can be of a type known per se and has one or more external threads 4a. The implant is screwed into a hole 6 formed in the bone. The implant is also provided with a top surface 4b against which the bearing surface 2a of the spacer is intended to bear when the spacer has been screwed into the implant by means of the screw 3. The implant also has an internal thread 4c with which the thread 3b of the screw can be screwed. The implant is also provided with a hexagon, by means of which the implant can be screwed down into the hole 6 formed in the dentine 5. FIG. 1 shows a position 7 in which the holder has been moved into position near the implant for cooperation between the threads 3b and 4c.

In accordance with FIG. 2, the spacer can be designed in a manner known per se. Thus, a bearing part 2b is included for the head 3c of the screw. The bearing recess of the part 2b for the screw head 3c is indicated by 2c. At the screw head 3c, the screw is also provided with a projecting flange or tabs 3d which cooperate with a top surface 2d of the spacer element. The part 1b of the holder is provided with an end recess 1e. The spacer 2 is introduced into this recess 1e. At the lower end, the spacer has a recess 2e. The end part 1b also has a second recess 1f in which the upper part of the screw head is introduced. The part 1b is also provided with an inwardly directed flange 1g or flange parts which can cooperate with the outside of the spacer part 2a. The spacer part 2a and the said inwardly projecting flange/flange parts are chosen so as to give a rotationally fixed anchoring for the spacer 2 in the part 1b. The recess 1f is chosen with a diameter dimension or a corresponding dimension in relation to a part 3e of the screw which projects into the recess 1f so as to give a rotationally fixed function. The recess 1f can be cylindrical or has a polygonal shape corresponding to the shape of the screw at the said inserted part 3e. The arrangement is thus such that both the spacer and the screw are given a rotationally fixed anchoring in the holder 1.

FIGS. 1 and 2 thus show that the holder with spacer and screw can be moved into a position of cooperation 7 with the implant such that the thread 3b engages in the internal thread 4c. The holder can thereafter be given rotating movements 8 which function as screwing movement for the screw 3 into the implant 1 via the threads 3b and 4c. By virtue of the fact that the spacer 2 and the screw 3 are rotationally fixed in the holder 1, screwing down can continue until the lower bearing surface 2a of the spacer contacts the upper bearing surface 4b of the implant. The securing function can be designed such that the force of the rotating movement 8 is maximized and such that the screw and the spacer slip in relation to the holder when this force reaches a certain value. Risks of loosening of the implant 4 in the bone 5 with the unit are thereby eliminated. The anchoring arrangement for the spacer 2 and the screw 3 in the holder is also such that when the screw 3 has been completely or partially threaded down into the implant, the holder can be released from the completely or partially inserted screw, and the spacer fixed loosely or firmly to the screw in the longitudinal direction with a loosening force F which essentially coincides with the longitudinal axis 1h of the holder and/or with an angle of rotational force F' upon whose application the holder disengages from the spacer and the screw by deflection of the holder material. The screw head 3c is thus exposed so that the groove 3f becomes accessible for another tool, for example a conventional screwdriver.

After the holder has been released, it can be discarded. Production of the holder is relatively inexpensive by virtue of the plastic material chosen. Only part of the holder needs to be made of plastic material, i.e. the part 1b which is intended to exert elasticity movements in the securing function for the screw and the spacer. The remainder of the holder can consist of re-usable material, and known joining members can be used between the parts 1a and 1b.

FIG. 3 shows the holder 1 and the spacer 2 and the screw 3 in separate positions. Upon assembly of spacer and screw in the holder (or vice versa), the screw and the spacer are joined in the position shown in FIG. 2, after which application to the holder or application of the holder to spacer and screw is effected. Holder, spacer and screw are preferably supplied in the state shown in FIG. 1. When screwing into the implant is effected using the holder, the latter is removed and discarded or re-used partially as described above. In FIG. 3, the member 3d' fixing the longitudinal direction has the form of a solid flange extending around the screw head. FIG. 3 also shows indents 2f and 2g on the spacer element, which indents can cooperate with the inwardly projecting flange 1g (FIG. 2) for forming nibs or snap-locking members included in the function for fixing the angle of rotation. FIG. 4 shows the annular bearing surface 2a in its entirety on the spacer 2. FIG. 4 also shows the absence of internal hexagon. Such an internal hexagon normally cooperates with the hexagon 4d of the implant (cf. FIG. 1). Such a hexagon or equivalent is not relevant in the present case for the reasons set out above. In FIG. 4, a counterstay function is also indicated by 9, which counterstay function can be activated when the screw 3 is being tightened.

In FIGS. 4a and 5, the snap-in function between spacer and holder is shown in greater detail. The indents on the spacer 2 are represented by the indents 2f and 2g. In the illustrative embodiment shown, there are six such recesses. The flange 1g which is shown enlarged in FIG. 5 in relation to the spacer 2 in FIG. 4a can thus be made to snap down into the indents after a deflection force F" has been added to a radial deflection movement in the same direction as the application force. When the flange 1g has snapped down into the indents, the surfaces 1d and 2d on the holder 1b and spacer 2, respectively, bear on each other. The parts 2h above the indents form nibs or snap-in members for the said flange 1g.

FIGS. 5 and 6 show the holder parts 1a and 1b and the recesses 1e and 1f. A radial annular surface is also indicated by 1h, which is essentially parallel to the annular end surface 1d. The surface 1h merges into the flange 1g. The wall of the recess 1f is indicated by 1k. The recesses 1e and 1f are cylindrical in the example shown.

The invention is not limited to the embodiment shown above by way of example, but can be modified within the scope of the inventive concept.

What is claimed is:

1. A method for securing a spacer to an implant integrated in bone, the method comprising:
   engaging a spacer and a screw with a single recess of a holder in a rotationally fixed position with respect to the holder, wherein the spacer is engaged in a spacer engaging portion of the recess and the screw is engaged in a screw engaging portion of the recess that is continuous with the spacer engaging portion;
   inserting the screw in a threaded receiving passage of the implant such that threads on the screw engage threads of the receiving passage;
   applying a rotational motion to the holder, thereby rotating the rotationally fixed spacer and screw and screwing the screw into the receiving passage of the implant;
   establishing cooperation between a bearing surface of the spacer and a top surface of the implant at a predetermined position of screwing; and
   separating the holder from the spacer and the screw.

2. The method according to claim 1, wherein the spacer includes a bearing surface that protrudes beyond the holder, and a threaded portion of the screw protrudes beyond the bearing surface.

3. The method according to claim 1, wherein a threaded portion of the screw extends through a recess in the spacer and a head of the screw cooperates with a tightening and locking surface on the spacer, and wherein the spacer comprises a bearing surface operable to cooperate with a top surface of the implant.

4. The method according to claim 1, further comprising:
   separating the holder from the spacer and the screw by applying a separating motion to the holder, thereby exposing the screw for further tightening.

5. The method according to claim 4, wherein the separating motion is distinct from the rotational movement to screw the screw into the implant.

6. The method according to claim 1, wherein to achieve a holding function between the holder, the spacer and the screw to form a common rotationally fixed unit, the screw is arranged against a tightening and locking surface of the spacer, and then the spacer and screw are arranged in an end recess if the holder or the holder is pressed over the spacer and the screw to rotationally fix the spacer and the screw in the holder.

7. The method according to claim 6, wherein the holder works with at least one of an elastic function, a spring function and a snap-in function operable to lock the spacer and the screw in a coupled position to the holder in the direction of rotation.

8. The method according to claim 6, wherein the spacer is brought into cooperation with the top surface of the implant only via an annular end surface.

9. The method according to claim 1, wherein the implant is integrated in jaw bone.

10. An arrangement operable to secure a spacer to an implant integrated in bone, the arrangement comprising:
    a holder operable to engage a spacer and a screw, the holder comprising
      a grip portion, and
      a recess comprising a spacer engaging portion and a screw engaging portion continuous with the spacer engaging portion, the spacer engaging portion operable to engage at least a portion of the spacer, the screw engaging portion operable to engage at least a portion of a head of the screw;
    wherein the holder supports the screw and the spacer in a rotationally fixed position and
    wherein the holder is separable from the spacer and the screw by means of a separating movement.

11. The arrangement according to claim 10, wherein the separation movement comprises applying a lateral force to the holder.

12. The arrangement according to claim 10, wherein the separation movement is distinct from the tightening movement.

13. The arrangement according to claim 10, wherein the screw is screwed into the implant to a position where a bearing surface of the spacer cooperates with the top surface of the implant.

14. The arrangement according to claim 10, wherein at least the screw engaging portion and the spacer engaging portion comprise plastic or other elastic and/or resilient material.

15. The arrangement according to claim 10, wherein the holder holds the screw and the spacer in a coupled position that prevents reciprocal rotating movements between the spacer, the screw and the holder.

16. The arrangement according to claim 15, wherein the couple position is obtained from clamping or spring function and/or guide surfaces and/or a snap-in function.

17. The arrangement according to claim 10, wherein the spacer engaging portion is operable to engage at least one securing part on the spacer.

18. The arrangement according to claim 17, wherein the screw and the spacer are secured on the holder by elasticity or resilience in a wall-supporting material of the first and second recesses.

19. The arrangement according to claim 10, wherein the grip portion comprises an elongate part made of plastic or equivalent material.

20. The arrangement according to claim 10, wherein the holder is comparatively easily separable from the spacer and the screw, in their position applied in or firmly screwed to the implant, by means of a withdrawal movement which essentially coincides with the longitudinal direction of the implant or rotating movement which is distinct from the screwing movement.

21. The arrangement according to claim 10, wherein the spacer comprises an annular bearing surface without internal guide surfaces.

22. The arrangement according to claims 10, wherein the holder and its attachment to the spacer and the screw are arranged to permit a first anchoring contact between the top surface of the implant and a bearing surface of the spacer which eliminates the risk of loosening of the implant in the bone, and, after the holder has been removed, the screw can be tightened to obtain a second anchoring contact which is effected with a force which considerably exceeds the force for the first anchoring contact.

23. The arrangement according to claim 22, wherein the second anchoring contact is effected by means of a counterstay function in the spacer.

24. The arrangement according to claim 10, wherein the thread of the screw is made of relatively strong material and/or is coated with a friction-reducing coating for the purpose of improving the anchoring stress between spacer, screw and implant.

25. The arrangement according to claim 10, wherein a thread diameter of the screw is substantially less than a diameter of a bearing surface of the spacer.

26. The arrangement according to claim 25, wherein the diameter of the screw thread, the diameter of the bearing surface of the spacer, and a low-friction material and/or low-friction coating are chosen to substantially lower the coefficient of friction at the thread as it is at the bearing surface, such that a secure counterstay can be applied against the outside of the spacer upon further tightening, despite the absence of mechanical locking via active locking surfaces between the spacer and the implant.

27. The arrangement according to claim 26, wherein the coefficient of friction is half as great.

28. The arrangement according to claim 10, wherein a thread diameter of the screw is half of a diameter of a bearing surface of the spacer.

29. The arrangement according to claim 10, wherein the spacer comprises a tightening and locking surface, a bearing surface operable to cooperate with a top surface of the implant and a screw receiving passage, and the screw comprises a threaded portion and a head portion operable to cooperate with the tightening and locking surface of the spacer, wherein the holder is operable to support the screw in a position passing through the screw receiving passage of the spacer with the bearing surface of the spacer protruding beyond the holder and the threaded portion of the screw protruding beyond the bearing surface of the spacer, wherein the holder supports the screw and the spacer such that the spacer and the screw can be applied to the implant in a position of cooperation between the threaded portion of the screw and a threaded portion of the implant, wherein applying a rotational force to the holder permits the threaded portion of the screw to be screwed into the threaded portion of the implant, and wherein the holder is separable from the spacer and the screw to expose the screw for possible further tightening.

30. An arrangement, comprising:

a spacer, a tightening screw for an implant integrated in bone; and a holder comprising a single recess including a spacer engaging portion and a screw engaging portion continuous with the spacer engaging portion, the recess being operable to retain the spacer and the screw for facilitating application of the spacer and screw to the implant, wherein the holder supports the spacer and the screw in a rotationally fixed manner, wherein a bearing surface of the spacer operable to bear against a top surface of the implant protrudes beyond the holder, and wherein the screw extends through the spacer and protrudes beyond the bearing surface.

31. The arrangement according to claim 30, wherein the spacer and the screw head assume rotationally fixed positions in the holder by virtue of the fact that the holder is made of resilient and/or elastic material at least at said recess, and the holder with resilient and/or elastic function cooperates with the spacer and the screw head.

32. The arrangement according to claim 30, wherein the rotationally fixed attachment is also effected by a snap-in function and wherein the spacer is designed with nibs and/or indents for the said snap-in function.

33. The arrangement according to claim 30, wherein upon positioning the spacer and the screw in the implant, the holder can be separated from the spacer and the screw head for longitudinal displacement in the longitudinal direction of the implant and/or a tilting movement.

34. The arrangement according to claim 30, wherein the holder, the spacer and the screw form a rotationally fixed unit, by means of which the thread of the screw can be screwed into the thread of the implant by screwing movements.

* * * * *